United States Patent
Zhong et al.

(10) Patent No.: US 10,617,679 B2
(45) Date of Patent: Apr. 14, 2020

(54) DEUTERATED COMPOUNDS AND MEDICAL USES THEREOF

(71) Applicant: JINGLUWEIDAI INFORMATION CONSULTING SERVICE (BEIJING) CO. LTD., Beijing (CN)

(72) Inventors: Bohua Zhong, Beijing (CN); Jianming Wang, Beijing (CN); Xuefeng Jin, Beijing (CN)

(73) Assignee: JINGLUWEIDAI INFORMATION CONSULTING SERVICE (BEIJING) CO. LTD., Beijing (CN)

(*) Notice: Subject to any disclaimer, the term of this patent is extended or adjusted under 35 U.S.C. 154(b) by 0 days.

(21) Appl. No.: 16/383,307

(22) Filed: Apr. 12, 2019

(65) Prior Publication Data

US 2019/0240204 A1    Aug. 8, 2019

Related U.S. Application Data

(63) Continuation-in-part of application No. PCT/CN2017/000607, filed on Sep. 22, 2017.

(30) Foreign Application Priority Data

Oct. 13, 2016  (CN) .......................... 2016 1 0890151

(51) Int. Cl.

| | |
|---|---|
| A61K 31/4745 | (2006.01) |
| A61K 31/4375 | (2006.01) |
| A61P 25/30 | (2006.01) |
| C07D 471/04 | (2006.01) |
| A61P 25/04 | (2006.01) |
| A61P 25/00 | (2006.01) |
| C07D 455/03 | (2006.01) |
| A61P 25/32 | (2006.01) |
| A61P 25/34 | (2006.01) |
| A61P 25/18 | (2006.01) |

(52) U.S. Cl.
CPC ...... *A61K 31/4375* (2013.01); *A61K 31/4745* (2013.01); *A61P 25/00* (2018.01); *A61P 25/04* (2018.01); *A61P 25/18* (2018.01); *A61P 25/30* (2018.01); *A61P 25/32* (2018.01); *A61P 25/34* (2018.01); *C07D 455/03* (2013.01); *C07D 471/04* (2013.01)

(58) Field of Classification Search
CPC .......................... A61K 31/4745; C07D 471/22
USPC ............................................. 514/284; 546/71
See application file for complete search history.

(56) References Cited

FOREIGN PATENT DOCUMENTS

JP    1975019788 A    3/1975

OTHER PUBLICATIONS

Zhang, Xin et al. "Preparation of 2H and 3H Labeled Tetrahyroprotoberberines", Nuclear Techniques, Apr. 30, 1988, p. 24-25, vol. 11, No. 4, Shanghai Institute of Maeria Medica, Academia Sinica, China. (English Abstract on p. 3).

*Primary Examiner* — Jeffrey H Murray
(74) *Attorney, Agent, or Firm* — Novick, Kim & Lee, PLLC; Allen Xue

(57) ABSTRACT

The present disclosure relates to a compound of Formula I or a non-toxic pharmaceutically acceptable salt or solvate thereof, wherein each R1, R2, R3, and R4 is independently selected from methyl ($-CH_3$) and trideuteromethyl ($-CD_3$), at least one of R1, R2, R3, and R4 is selected from trideuteromethyl ($-CD_3$).

The compound is a deuterated derivative of L-tetrahydropalmatine, which not only markedly improves pharmacological effects, but also significantly reduces cardiac side effects, liver toxicity, and remarkably decreases individual differences.

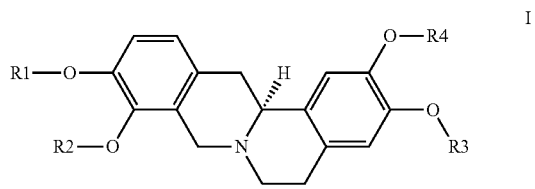

7 Claims, No Drawings

DEUTERATED COMPOUNDS AND MEDICAL USES THEREOF

FIELD OF THE INVENTION

The present disclosure relates to a novel deuterated derivative of L-tetrahydropalmatine or a pharmaceutically acceptable salt or solvate thereof, a pharmaceutical composition comprising the compound as active ingredient, and a use of the derivative or a pharmaceutically acceptable salt or solvate thereof in the preparation of psychotropic drug.

BACKGROUND OF THE INVENTION

L-tetrahydropalmatine (THP), also known as rotundine, which is an alkaloid extracted from dried tubers of the plant Corydalis, a member of the poppy family, having various therapeutic effects such as sedation, hypnosis and analgesia, clinically useful in the treatment of headache, menstrual pain and insomnia.

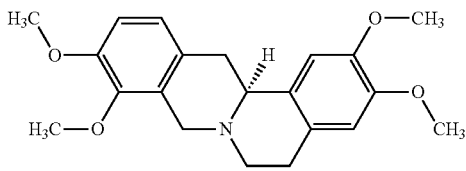

L-tetrahydropalmatine

Recent studies have found that L-tetrahydropalmatine has better analgesic effects on neuropathic pain (NPP), inflammatory pain, cancer-induced pain and antitumor drug-induced pain. Taking L-tetrahydropalmatine for long periods of time does not lead to addiction, and has better effect on overcoming cocaine addiction, methamphetamine addiction, opioid or drug addiction, alcohol addiction, smoking addition, etc.

However, L-tetrahydropalmatine leads to cardiac side effects such as reducing blood pressure, slowing heart rate, etc. It can also cause hepatotoxicity such as elevated transaminases, etc. Moreover, great individual differences in the effects of L-tetrahydropalmatine cause the uncontrollability of safety and efficacy of drugs.

The present disclosure relates to novel deuterated derivatives of L-tetrahydropalmatine. These deuterated derivatives not only markedly improve pharmacological effects, but also significantly reduce cardiac side effects, hepatotoxicity, and remarkably decrease individual differences.

DETAILED DESCRIPTION OF THE INVENTION

The present disclosure provides a compound of Formula I or a pharmaceutically acceptable salt or solvate thereof:

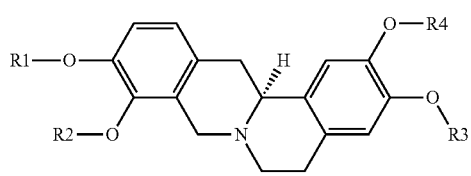

wherein each R1, R2, R3, and R4 is independently selected from methyl (—CH$_3$) and trideuteromethyl (—CD$_3$), at least one of R1, R2, R3, and R4 is selected from trideuteromethyl (—CD$_3$).

For example, the compound of Formula I or the pharmaceutically acceptable salt or solvate thereof, selected from the group consisting of compounds having the following structures:

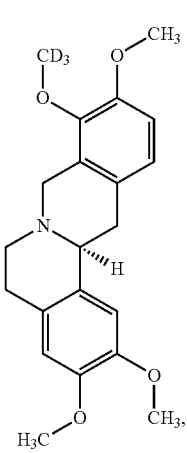

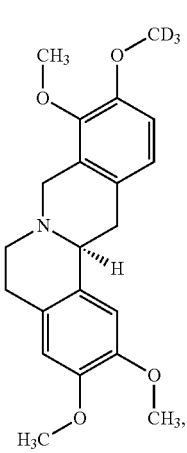

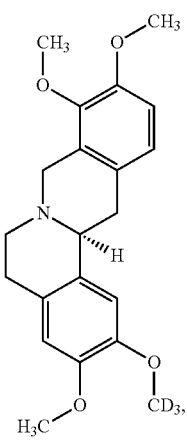

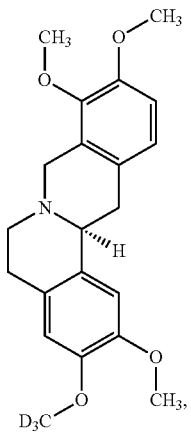
I₃

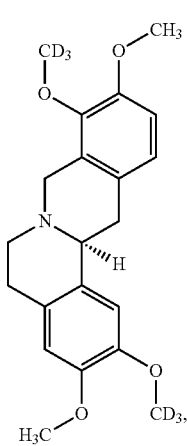
I₅

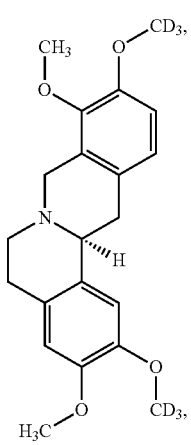
I₆

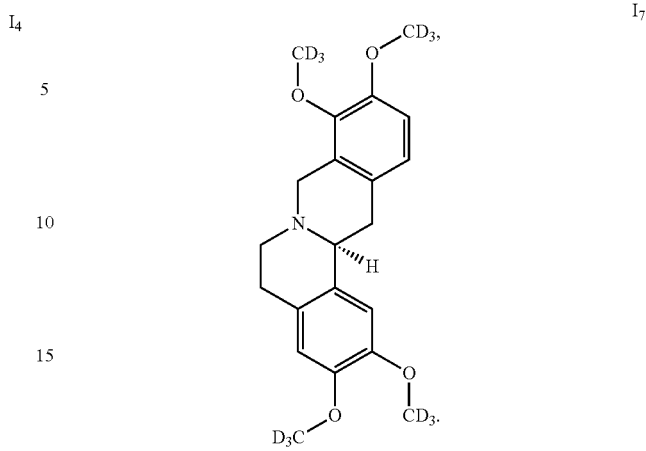
I₄, I₇

The present disclosure also provides a pharmaceutical composition containing the compound of Formula I, for example, the compound of Formula $I_1$, $I_2$, $I_3$, $I_4$, $I_5$, $I_6$ or $I_7$, or a non-toxic pharmaceutically acceptable salt or solvate thereof as an active ingredient, and a suitable excipient. The pharmaceutical compositions may be solutions, tablets, capsules or injections; and the pharmaceutical compositions may be administered by injection or administered orally.

The present disclosure also provides the use of the compound of Formula I or a non-toxic pharmaceutically acceptable salt or solvate thereof in the preparation of psychotropic drug. The compound of Formula I, for example, is selected from Formula $I_1$, $I_2$, $I_3$, $I_4$, $I_5$, $I_6$ or $I_7$.

Furthermore, the present disclosure also provides the use of a compound of Formula I or a non-toxic pharmaceutically acceptable salt or solvate thereof in the preparation of drug for the treatment of a algesic disease, such as inflammation-induced pain, cancer-induced pain, and antitumor drug-induced pain. For example, the compound is selected from Formula $I_1$, $I_2$, $I_3$, $I_4$, $I_5$, $I_6$ or $I_7$.

Furthermore, the present disclosure also provides use of the a compound of Formula I or a non-toxic pharmaceutically acceptable salt or solvate thereof in the preparation of drug for the treatment of an addictive disease, such as cocaine addiction, methamphetamine addiction, opioid or drug addiction, alcohol addiction, smoking addiction, ketamine addiction. For example, the compound is selected from Formula $I_1$, $I_2$, $I_3$, $I_4$, $I_5$, $I_6$ or $I_7$.

The present disclosure also provides a method for treating mental illness, wherein the method comprises administering an effective amount of the compound of Formula I, for example, the compound of Formula $I_1$, $I_2$, $I_3$, $I_4$, $I_5$, $I_6$ or $I_7$, or a non-toxic pharmaceutically acceptable salt or solvate thereof.

The present disclosure also provides a method for treating a algesic disease, wherein the method comprises administering an effective amount of the compound of Formula I, for example, the compound of Formula $I_1$, $I_2$, $I_3$, $I_4$, $I_5$, $I_6$ or $I_7$, or a non-toxic pharmaceutically acceptable salt or solvate thereof. The pain is such as inflammation-induced pain, cancer-induced pain, and antitumor drug-induced pain.

The present disclosure also provides a method for treating an addictive disease, wherein the method comprises administering an effective amount of the compound of Formula I, for example, the compound of Formula $I_1$, $I_2$, $I_3$, $I_4$, $I_5$, $I_6$ or $I_7$, or a non-toxic pharmaceutically acceptable salt or solvate thereof. The addictive disease is such as cocaine addiction, methamphetamine addiction, opioid or drug addiction, alcohol addiction, smoking addiction, ketamine addiction.

EXAMPLES

The present disclosure will be further illustrated with the following examples; however, the scope of the disclosure is not limited to the examples described below. Those skilled in the art will appreciate that various changes and modifications to the examples can be made without departing from the spirit and scope of the disclosure.

Example 1 Synthesis of (13a S)-2,3,10-trimethoxy-9-[(trideutero)-methoxy]-6,8,13,13a-tetrahydro-5H-isoquinolino[2,1-b]isoquinoline (I$_1$)

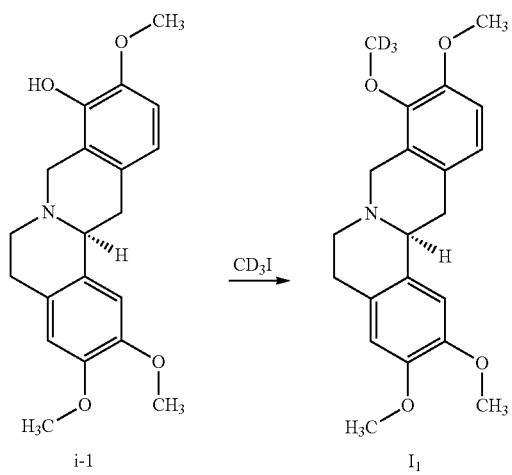

341 mg (1 mmol) of (13a S)-2,3,10-trimethoxy-6,8,13,13a-tetrahydro-5H-isoquinolino[2,1-b]isoquinoline-9-ol (i-1) was added to 5 ml of dimethylformamide and dissolved under stirring; then 280 mg (2 mmol) of potassium carbonate was added, and 290 mg (2 mmol) of CD$_3$I was added dropwise under stirring. The reaction mixture was stirred at 50° C. for 15 hours. The solid was filtered off and the filtrate was evaporated to dryness under reduced pressure, then separated by silica gel column chromatography, eluted with dichloromethane:methanol (10:1). The desired component was collected and evaporated to dryness under reduced pressure to give 130 mg of I$_1$. $^1$H-NMR (400 MHz, CDCl$_3$): 6.83 (s, 1H), 6.78 (d, 1H), 6.71 (d, 1H), 6.65 (s, 1H), 4.32 (d, 1H), 3.88 (s, 3H), 3.85 (s, 3H), 3.81 (s, 1H), 3.59-3.50 (m, 2H), 3.24 (dd, 1H), 3.21-3.10 (m, 2H), 2.83 (dd, 1H), 2.70-2.65 (m, 2H).

Example 2 Synthesis of (13a S)-2,3,9-trimethoxy-10-[(trideutero)-methoxy]-6,8,13,13a-tetrahydro-5H-isoquinolino[2,1-b]isoquinoline (I$_2$)

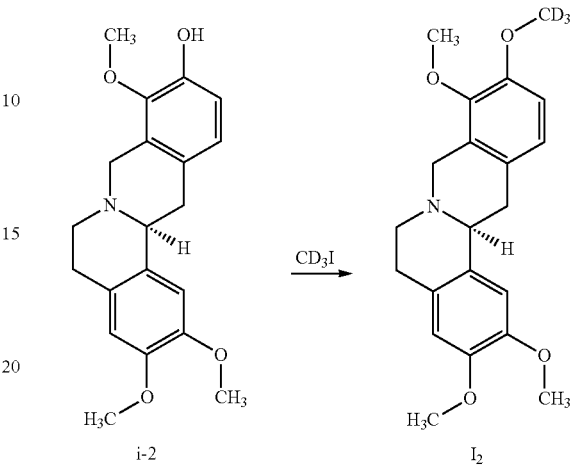

Referring to Example 1, i-1 was replaced with (13a S)-2,3,9-trimethoxy-6,8,13,13a-tetrahydro-5H-isoquinolino[2,1-b]isoquinoline-10-ol (i-2), which reacted with CD$_3$I in the presence of potassium carbonate. The obtained mixture was separated by silica gel column chromatography to give 105 mg of I$_2$. $^1$H-NMR (400 MHz, CDCl$_3$): 6.81 (s, 1H), 6.79 (d, 1H), 6.72 (d, 1H), 6.64 (s, 1H), 4.30 (d, 1H), 3.85 (s, 3H), 3.82 (s, 3H), 3.74 (s, 1H), 3.60-3.50 (m, 2H), 3.25 (dd, 1H), 3.20-3.10 (m, 2H), 2.81 (dd, 1H), 2.71-2.65 (m, 2H).

Example 3 Synthesis of (13a S)-3,9,10-trimethoxy-2-[(trideutero)-methoxy]-6,8,13,13a-tetrahydro-5H-isoquinolino[2,1-b]isoquinoline (I$_3$)

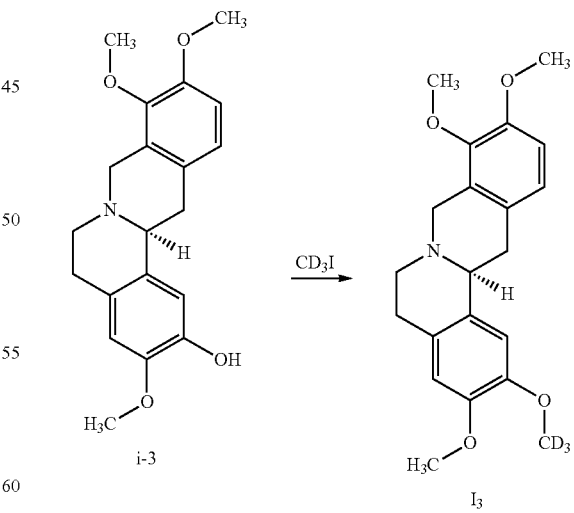

Referring to Example 1, i-1 was replaced with (13aS)-3,9,10-trimethoxy-6,8,13,13a-tetrahydro-5H-isoquinolino[2,1-b]isoquinoline-2-ol (i-3), which reacted with CD$_3$I in the presence of potassium carbonate. The obtained mixture was separated by silica gel column chromatography to give 85 mg of I₃. ¹H-NMR (400 MHz, CDCl₃): 6.86 (s, 1H), 6.79 (d, 1H), 6.75 (d, 1H), 6.68 (s, 1H), 4.35 (d, 1H), 3.86 (s, 3H), 3.81 (s, 3H), 3.61 (s, 1H), 3.55-3.50 (m, 2H), 3.22 (dd, 1H), 3.08-3.10 (m, 2H), 2.84 (dd, 1H), 2.70-2.65 (m, 2H).

Example 4 Synthesis of (13a S)-2,9,10-trimethoxy-3-[(trideutero)-methoxy]-6,8,13,13a-tetrahydro-5H-isoquinolino[2,1-b]isoquinoline (I₄)

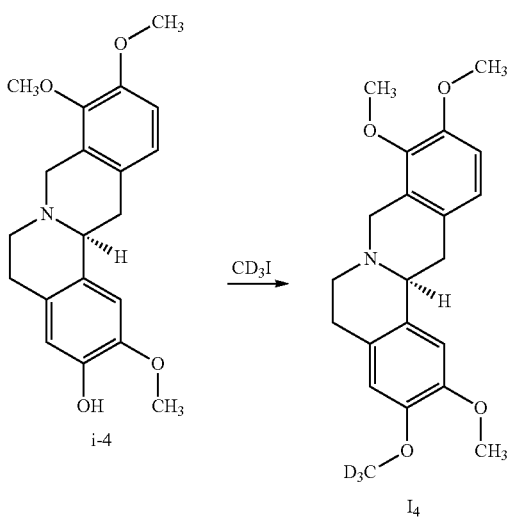

Referring to Example 1, i-1 was replaced with (13aS)-2,9,10-trimethoxy-6,8,13,13a-tetrahydro-5H-isoquinolino[2,1-b]isoquinoline-3-ol (i-4), which reacted with CD₃I in the presence of potassium carbonate. The obtained mixture was separated by silica gel column chromatography to give 92 mg of 14. ¹H-NMR (400 MHz, CDCl₃): 6.90 (s, 1H), 6.82 (d, 1H), 6.75 (d, 1H), 6.65 (s, 1H), 4.38 (d, 1H), 3.89 (s, 3H), 3.86 (s, 3H), 3.68 (s, 1H), 3.56-3.51 (m, 2H), 3.25 (dd, 1H), 3.22-3.13 (m, 2H), 2.82 (dd, 1H), 2.71-2.68 (m, 2H).

Example 5 Synthesis of (13a S)-3,10-dimethoxy-2,9-di-[(trideutero)-methoxy]-6,8,13,13a-tetrahydro-5H-isoquinolino[2,1-b]isoquinoline (I₅)

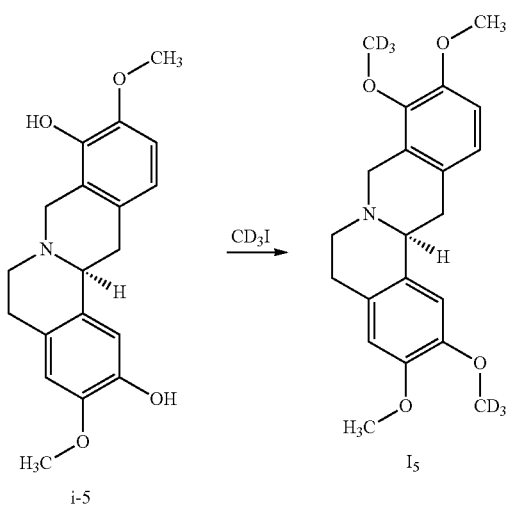

327 mg (1 mmol) of (13a S)-3,10-dimethoxy-6,8,13,13a-tetrahydro-5H-isoquinolino[2,1-b]isoquinoline-2,9-diol (i-5) was added to 5 ml of dimethylformamide and dissolved under stirring; then 560 mg (4 mmol) of potassium carbonate was added, and 435 mg (3 mmol) of CD₃I was added dropwise under stirring. The reaction mixture was stirred at 50° C. for 15 hours. The solid was filtered off and the filtrate was evaporated to dryness under reduced pressure, then separated by silica gel column chromatography and eluted with dichloromethane:methanol (10:1). The desired component was collected and evaporated to dryness under reduced pressure to give 115 mg of I₅. ¹H-NMR (400 MHz, CDCl₃): 6.88 (s, 1H), 6.77 (d, 1H), 6.73 (d, 1H), 6.61 (s, 1H), 4.32 (d, 1H), 3.87 (s, 3H), 3.80 (s, 1H), 3.52-3.50 (m, 2H), 3.21 (dd, 1H), 3.17-3.10 (m, 2H), 2.80 (dd, 1H), 2.68-2.63 (m, 2H).

Example 6 Synthesis of (13a S)-3,9-dimethoxy-2,10-di-[(trideutero)-methoxy]-6,8,13,13a-tetrahydro-5H-isoquinolino[2,1-b]isoquinoline (I₆)

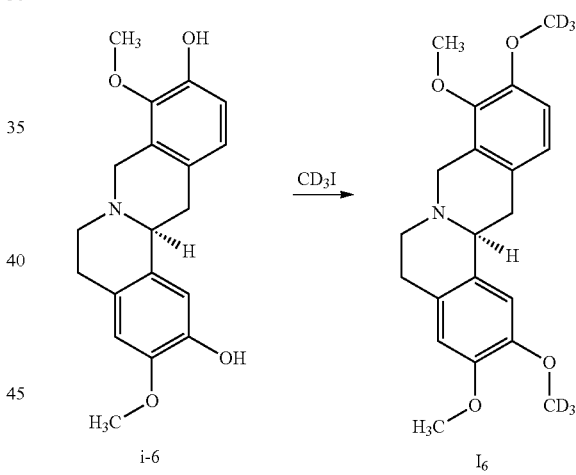

Referring to Example 5, i-5 was replaced with (13aS)-3,9-dimethoxy-6,8,13,13a-tetrahydro-5H-isoquinolino[2,1-b]isoquinoline-2,10-diol (i-6), which reacted with CD₃I in the presence of potassium carbonate. The obtained mixture was separated by silica gel column chromatography to give 100 mg of I₆. ¹H-NMR (400 MHz, CDCl₃): 6.83 (s, 1H), 6.78 (d, 1H), 6.71 (d, 1H), 6.65 (s, 1H), 4.32 (d, 1H), 3.88 (s, 3H), 3.81 (s, 1H), 3.59-3.50 (m, 2H), 3.24 (dd, 1H), 3.21-3.10 (m, 2H), 2.83 (dd, 1H), 2.70-2.65 (m, 2H).

Example 7 Synthesis of (13a S)-2,3,9,10-tetra-[(trideutero)-methoxy]-6,8,13,13a-tetrahydro-5H-isoquinolino[2,1-b]isoquinoline (I₇)

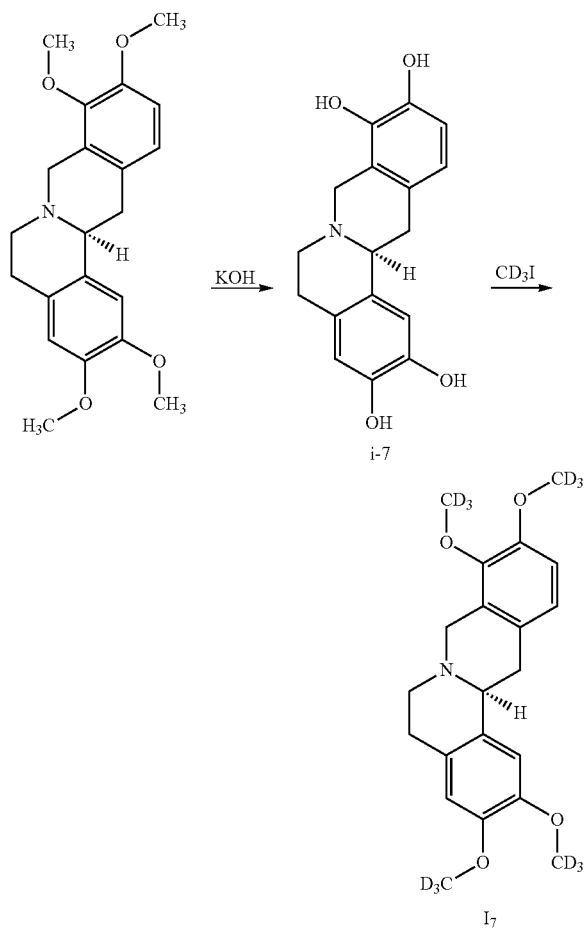

After 60 g of diethylene glycol was added into in a 100 mL reaction flask and stirred under nitrogen flow, 7 g of potassium hydroxide was added. When the temperature was raised to 80° C., another portion of 7 g potassium hydroxide was added. After all of potassium hydroxide was dissolved and the temperature was raised to 210° C., the water was removed. When the temperature was constant, 3.55 g (10 mmol) of L-tetrahydropalmatine was added and heated at 205-210° C. for 1.5 h. The reaction mixture was then poured into crushed ice, and neutralized to pH 8-9 with solid ammonium chloride to afford a solid precipitate. The precipitated solid was filtered, separated by silica gel column chromatography and eluted with dichloromethane:methanol (2:1). The desired component was collected and evaporated to dryness under reduced pressure to give 1.1 g of i-7.

900 mg (3 mmol) of i-7 was added to 10 ml of dimethylformamide and dissolved under stirring; then 2.0 g (15 mmol) of potassium carbonate was added, and 2.2 g (15 mmol) of CD₃I was added dropwise under stirring. The reaction mixture was stirred at 50° C. for 15 hours. The solid was filtered off and the filtrate was evaporated to dryness under reduced pressure, then separated by silica gel column chromatography and eluted with dichloromethane:methanol (10:1). The desired component was collected and evaporated to dryness under reduced pressure to give 120 mg of 17. $^1$H-NMR (400 MHz, CDCl₃): 6.87 (s, 1H), 6.75 (d, 1H), 6.70 (d, 1H), 6.61 (s, 1H), 4.30 (d, 1H), 3.61-3.50 (m, 2H), 3.23 (dd, 1H), 3.17-3.05 (m, 2H), 2.81 (dd, 1H), 2.72-2.67 (m, 2H).

Example 8 Evaluation of Analgesic Effects of Intragastrical Administration in a Rat Formalin Model SD rats (male, weight 160-180 g) were randomly divided into groups with 6 rats in each group. After the rats were intragastrically administered different doses separately, they were placed in PVC observation boxes for habituation. After 30 min, the rats were injected subcutaneously with 20 μL of 2.7% formalin solution into the plantar surface of the left hind paws, and quickly put back in the PVC observation boxes for observation. The length of time the rats spent licking the injected-formalin paws at the early response (0-5 min, phase I) and the late response (15-30 min, Phase II) was recorded, and the analgesic activities of the test compounds were evaluated according to the length of time the rats spent licking during the period of observation. The experimental data were expressed as mean±standard deviation. The shorter the licking time, the better the analgesic effect of the compound. The results are shown in Table 1:

TABLE 1

Analgesic effects of intragastric administration in a rat formalin model

| Drug | Dose (mg/kg) | Reaction time for phase I (sec) | Reaction time for Phase II (sec) |
| --- | --- | --- | --- |
| Solvent |  | 79.3 ± 10.7 | 218.7 ± 12.7 |
| THP | 20 | 86.8 ± 37.3 | 185.2 ± 39.7 |
|  | 40 | 40.6 ± 28.3* | 97.5 ± 33.6* |
| I₁ | 20 | 82.4 ± 33.2 | 194.0 ± 35.7 |
|  | 40 | 42.6 ± 45.0* | 92.7 ± 25.1* |
| I₂ | 20 | 82.1 ± 16.3 | 64.5 ± 19.5** |
|  | 40 | 41.0 ± 10.7 | 46.5 ± 16.0** |
| I₃ | 20 | 79.6 ± 31.3 | 126.3 ± 29.6 |
|  | 40 | 45.1 ± 29.4 | 72.3 ± 37.8** |
| I₄ | 20 | 90.3 ± 29.0 | 151.2 ± 31.6 |
|  | 40 | 61.5 ± 36.6 | 74.3 ± 38.0 |
| I₅ | 20 | 85.8 ± 28.0 | 112.7 ± 29.2* |
|  | 40 | 53.4 ± 23.5* | 66.5 ± 27.6** |
| I₆ | 20 | 41.9 ± 9.2** | 66.7 ± 8.7** |
|  | 40 | 38.6 ± 9.4** | 40.3 ± 9.0** |
| I₇ | 20 | 45.2 ± 9.9** | 58.2 ± 12.5** |
|  | 40 | 35.7 ± 9.0** | 35.9 ± 13.6** |

Compared with solvent group, *P < 0.05, **P < 0.01.

Example 9 Evaluation of Analgesic Effects of Intragastric Administration in a Rat Chronic Sciatic Nerve Compression Neuralgia Model SD rats (male, weight 160-180 g) were anesthetized using sodium pentobarbital (40 mg/kg), of which the sciatic nerves were separated in the middle segment of the right hind limbs. In the anterior segment of the sciatic nerve to be bifurcated, the sciatic nerve was separated from the surrounding tissue using a sterile glass hook. Four rings were loosely ligated with sterile chrome gut (No. 4, 0.15 mm in diameter) by an interval of 1 to 2 mm. Topically sprinkled with penicillin powder. The muscle tissue and skin were sutured. The rats were placed in a cage with cork dust. In the sham surgery group, the sciatic nerve was only exposed, and the other treatments were the same as described above. The rats after surgery were placed in a metal cage. The footpads of the rats were stimulated with different weights of fiber filaments with stimulus intervals of 5 seconds, until the fiber filament was found that elicits four to six foot-lifting reactions in rats during 10 stimulations. The weight of the filament was recorded and set to be the threshold (in g). Meanwhile, the number of foot-lifting response to the 10 stimulations of the fiber filaments of different weights was recorded, and the highest threshold was set at 26 g.

5-6 rats in each group were intragastrically administered and the pain thresholds were measured 1 hour after administration. Statistical analysis of the thresholds was performed using non-parametric Wilcoxon 2-Sample Test and Kruskal-Wallis Test, and the data was analyzed with SASS data processing software.

Analgesic percent (%)=(pain threshold after drug treatment–pain threshold before drug treatment)/(maximal analgesia threshold–pain threshold before drug treatment)×%.

The experimental results are shown in Table 2.

TABLE 2

Analgesic effects of intragastric administration in a rat chronic sciatic nerve compression neuralgia model

| Drug | Dose (mg/kg) | Analgesic percent (%) |
|---|---|---|
| THP | 20 | 27.41 |
|  | 40 | 68.36 |
| $I_2$ | 20 | 59.00 |
|  | 40 | 68.86 |
| $I_3$ | 20 | 44.80 |
|  | 40 | 68.67 |
| $I_5$ | 20 | 39.40 |
|  | 40 | 67.56 |
| $I_6$ | 20 | 63.80 |
|  | 40 | 69.12 |
| $I_7$ | 20 | 70.67 |
|  | 40 | 73.53 |

Example 10 Inhibition of Oxycodone-Induced Place Preference in Rats

SD rats (male, weight 160-180 g) were placed in conditioned place preference (CPP) training boxes, where the partition door between the boxes was open. Time the rats spent in each of the boxes was recorded within 15 min in order to determine the natural tendency of the rats. The rats were then randomly divided into groups with 10 rats in each group according to the amount of time spent in the white box. The white box was a drug box, and the black box was a box with the absence of the drug. After intragastric administration with a test compound for 40 minutes, the rats were injected subcutaneously with oxycodone (2.5 mg/kg, s.c.) or saline, and immediately placed in the white box or the black box to be trained for 45 minutes, once a day for 9 consecutive days. On the 10th day, the rats were placed in the training boxes with the partition door open. The time the rats spent in the white box was recorded within 15 minutes to evaluate effects on place preference in the rats. The experimental results are shown in Table 3.

TABLE 3

Inhibition of oxycodone-induced place preference in rats

| Drug | Test dose (mg/kg) | Time spent in the drug box (Mean ± S, s) |
|---|---|---|
| Solvent |  | 112.11 ± 32.23 |
| oxycodone + saline |  | 365.02 ± 23.06 |
| oxycodone + THP | 10 | 253.23 ± 77.14 |
|  | 20 | 157.04 ± 60.6** |
| oxycodone + $I_2$ | 10 | 193.94 ± 44.3* |
|  | 20 | 140.59 ± 28.52** |
| oxycodone + $I_6$ | 10 | 183.27 ± 33.97* |
|  | 20 | 129.35 ± 23.66** |
| oxycodone + $I_7$ | 10 | 154.32 ± 21.38** |
|  | 20 | 135.40 ± 25.09** |

Compared with solvent group,
*$P < 0.05$,
**$P < 0.01$.

Example 11 Effects on Blood Pressure and Heart Rate in Rats

SD rats (male, weight 160-180 g) were fasted for 12 hours before administration but had free access to drinking water. The rats were randomly divided into groups. They were anesthetized with an intraperitoneal injection of 50-60 mg/kg dose of sodium pentobarbital. Each rat was fixed on the back on the surgical table. The skin was cut from the center of the neck, and an incision of about 2.5 cm was made. The subcutaneous tissue and the median muscle were separated; the trachea was fully exposed; and the endotracheal intubation was performed. The subcutaneous tissue was separated from front to back on the right side; the right common carotid artery, the vagus nerve and the sympathetic nerve were exposed; and the carotid artery cannulation was performed. Finally, the endotracheal tube and the carotid artery cannula were respectively connected to a respiration transducer and a blood pressure transducer, and then connected to a multifunctional physiological recorder. At 30 minutes after surgery, the rats were intragastrically administrated. Heart rate and blood pressure were measured at different time points after administration. The results are shown in Tables 4 and 5, respectively.

TABLE 4

Effects on blood pressure in rats

| Drug | Dose (mg/kg) | Blood pressure (mmHg) | | | | | |
|---|---|---|---|---|---|---|---|
|  |  | 0 | 30 | 60 | 90 | 120 | 180 |
| Solvent |  | 114.0 ± 11.4 | 112.3 ± 10.3 | 109.2 ± 8.8 | 109.3 ± 9.0 | 118.6 ± 12.6 | 115.0 ± 10.6 |
| THP | 20 | 111.5 ± 11.5 | 109.4 ± 20.6 | 105.00 ± 28.21 | 105.1 ± 20.0 | 112.7 ± 19.3 | 113.3 ± 18.3 |
|  | 40 | 114.2 ± 14.6 | 98.0 ± 30.1 | 81.63 ± 28.8* | 79.00 ± 28.2* | 91.6 ± 24.7* | 97.3 ± 14.5 |

TABLE 4-continued

Effects on blood pressure in rats

| Drug | Dose (mg/kg) | Blood pressure (mmHg) | | | | | |
|---|---|---|---|---|---|---|---|
| | | 0 | 30 | 60 | 90 | 120 | 180 |
| $I_2$ | 20 | 113.1 ± 15.7 | 113.4 ± 17.3 | 101.5 ± 27.46 | 102.25 ± 21.6 | 113.1 ± 14.2 | 102.3 ± 7.6 |
| | 40 | 114.6 ± 19.4 | 95.5 ± 15.9* | 82.5 ± 19.8* | 92.8 ± 18.6* | 110.5 ± 15.5 | 100.0 ± 17.8 |
| $I_6$ | 20 | 115.6 ± 21.9 | 108.5 ± 10.75 | 102.0 ± 11.4 | 104.7 ± 10.70 | 110.5 ± 6.8 | 106.5 ± 13.7 |
| | 40 | 111.0 ± 21.4 | 95.4 ± 14.5* | 83.5 ± 10.30* | 85.2 ± 8.0* | 110.00 ± 11.6 | 109.5 ± 14.1 |
| $I_7$ | 20 | 112.6 ± 27.5 | 103.4 ± 11.7 | 104.2 ± 9.8 | 102.6 ± 7.2 | 114.1 ± 11.3 | 135.3 ± 15.6 |
| | 40 | 113.0 ± 11.4 | 92.4 ± .10.4* | 83.5 ± 7.2* | 82.6 ± 6.5* | 95.3 ± 9.5* | 101.8 ± 8.1 |

Compared with solvent group, *P < 0.05, **P < 0.01.

TABLE 5

Effects on heart rate in rats

| Drug | Dose (mg/kg) | Heart rate (BTM) | | | | | |
|---|---|---|---|---|---|---|---|
| | | 0 | 30 | 60 | 90 | 120 | 180 |
| Solvent | | 407.1 ± 34.2 | 401.3 ± 32.3 | 409.5 ± 31.6 | 406.8 ± 20.1 | 398.8 ± 28.3 | 412.0 ± 22.2 |
| THP | 20 | 399.3 ± 32.6 | 377.1 ± 52.3 | 387.3 ± 50.5 | 399.8 ± 60.7 | 408.8 ± 55.9 | 429.8 ± 25.5 |
| | 40 | 391.8 ± 32.9 | 372.1 ± 46.5 | 329.0 ± 63.2* | 340.0 ± 71.4* | 372.0 ± 64.6* | 400.0 ± 30.5 |
| $I_2$ | 20 | 400.8 ± 32.1 | 378.3 ± 30.3 | 384.6 ± 48.2 | 388.0 ± 21.4 | 402.5 ± 59.3 | 407.0 ± 36.5 |
| | 40 | 409.2 ± 41.7 | 390.7 ± 41.7 | 319.7 ± 57.2* | 353.8 ± 66.7* | 378.0 ± 47.6* | 407.0 ± 42.6 |
| $I_6$ | 20 | 407.1 ± 43.4 | 400.2 ± 29.4 | 401.0 ± 28.47 | 403.0 ± 30.2 | 396.7 ± 36.3 | 402.5 ± 28.8 |
| | 40 | 414.1 ± 37.6 | 375.8 ± 29.3 | 362.8 ± 20.7* | 367.2 ± 27.0* | 393.5 ± 34.6 | 380.8 ± 30.5 |
| $I_7$ | 20 | 401.5 ± 32.1 | 380.8 ± 33.4 | 389.5 ± 26.6 | 405.3 ± 31.0 | 391.0 ± 24.9 | 398.5 ± 28.8 |
| | 40 | 407.9 ± 29.5 | 366.8 ± 27.7 | 332.6 ± 24.9* | 343.2 ± 21.0* | 356.7 ± 25.8* | 362.0 ± 32.1 |

Compared with solvent group, *P < 0.05, **P < 0.01.

Example 12 Evaluation of Subacute Toxicity

Male Wistar rats were randomly divided into groups with 10 rats in each group and weighed. A certain concentration of a test sample was ground and suspended in a 0.5% sodium carboxymethyl cellulose solution. The sodium carboxymethyl cellulose suspension containing 40 mg/kg of the test compound and a blank sodium carboxymethyl cellulose suspension as a control were intragastrically administered, once a day for 14 consecutive days. After the last administration, the rats were fasted but had free access to drinking water for 12 hours, and then anesthetized. Their blood samples were obtained from the abdominal aortas. According to SOPB093 "Standard Operating Procedures for Serum Preparation" in National Beijing Center for Drug Safety Evaluation and Research, serum was prepared for the determination of blood biochemical and immunological indicators; according to SOPB032 "Preparation of vacuum tubes with EDTA anticoagulation", EDTA anticoagulation was prepared for the general blood routine tests.

The results showed that weight gain and food consumption in the animals in each drug group were lower than those in the solvent control group, but there was no statistical difference. The test results of 14 hematological indices and 15 biochemical blood plasma indicators showed that there was a significant increase in plasma ALT and AST in Rotundine group, $I_2$ and $I_6$ groups, and no significant difference between $I_7$ group and the control group in plasma ALT and AST. All other indicators were within normal ranges. The histopathological examination showed that vacuolar degeneration of hepatocytes at the peripheral and the middle zones of the hepatic lobules in Rotundine group, $I_2$ and $I_6$ groups was observed, and a small focal to a large patche of coagulative necrosis of hepatocytes occurred in the individual animals.

TABLE 6

Effects on transaminase in rats

| Dose | ALT(U/L) | AST(U/L) |
|---|---|---|
| Normal control | 67.0 ± 9.8 | 122.0 ± 24.6 |
| THP | 160.0 ± 70.6* | 216.8 ± 91.6* |
| $I_2$ | 172.8 ± 37.5* | 195.0 ± 32.1* |
| $I_6$ | 165.3 ± 38.0* | 251.8 ± 32.0* |
| $I_7$ | 84.5 ± 20.6 | 143.8 ± 21.0 |

Compared with normal group, *P < 0.05.

The invention claimed is:

1. A compound of formula I or a pharmaceutically acceptable salt or solvate thereof:

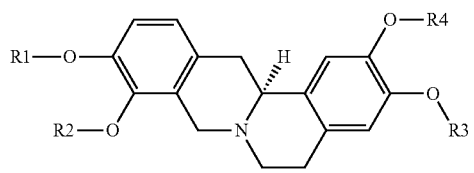

wherein each R1, R2, R3, and R4 is independently selected from methyl (—CH$_3$) and trideuteromethyl (—CD$_3$), and at least one of R1, R2, R3, and R4 is trideuteromethyl (—CD$_3$).

2. The compound according to claim 1 or a pharmaceutically acceptable salt or solvate thereof, wherein the compound of formula I is selected from:

I₁
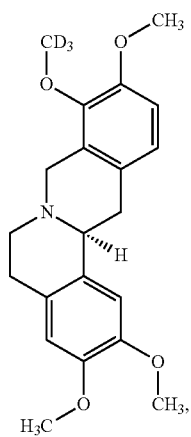
I₂
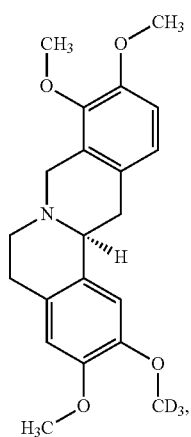
I₃
I₄
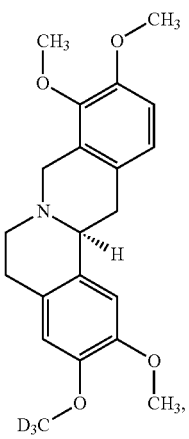
I₅
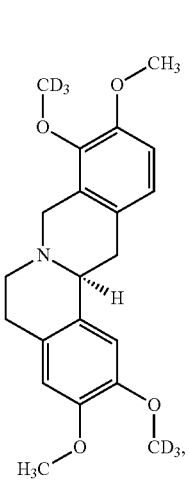
I₆
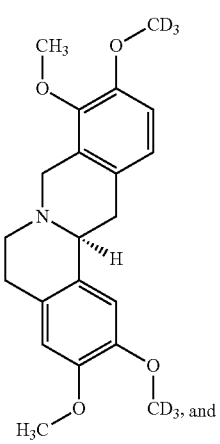

-continued

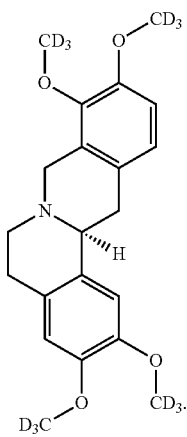

I₇

3. A pharmaceutical composition comprising the compound according to claim 1 or a pharmaceutically acceptable salt or solvate thereof as an active ingredient, and a suitable excipient.

4. The pharmaceutical composition according to claim 3, wherein the composition is in the form of a solution, a tablet, a capsule, or an injection.

5. A method for treating a disease, wherein said method comprises administering an effective amount of the compound of claim 1, or a non-toxic pharmaceutically acceptable salt or solvate thereof, and said disease is a mental illness, an algesic disease, or an addictive disease.

6. The method according to claim 5, wherein said algesic disease is inflammation-induced pain, cancer-induced pain, or antitumor drug-induced pain.

7. The method according to claim 5, wherein said addictive disease is cocaine addiction, methamphetamine addiction, opioid or drug addiction, alcohol addiction, smoking addiction, or ketamine addiction.

* * * * *